United States Patent [19]

Brandes et al.

[11] 4,178,383
[45] Dec. 11, 1979

[54] FUNGICIDALLY ACTIVE OXIME-ETHERS OF ISONITROSOCYANOACETAMIDES

[75] Inventors: Wilhelm Brandes, Cologne; Werner Daum, Krefeld; Peter Kraus, Cologne, all of Fed. Rep. of Germany

[73] Assignee: Bayer Aktiengesellschaft, Leverkusen, Fed. Rep. of Germany

[21] Appl. No.: 796,503

[22] Filed: May 12, 1977

[30] Foreign Application Priority Data

May 28, 1976 [DE] Fed. Rep. of Germany ........ 2623847
Dec. 16, 1976 [DE] Fed. Rep. of Germany ........ 2657145

[51] Int. Cl.² .................. C07C 121/52; C07C 121/66; A01N 9/20
[52] U.S. Cl. ................................. 424/304; 260/389; 260/464; 260/465 D
[58] Field of Search ................. 260/465 D, 465.4; 424/304

[56] References Cited

U.S. PATENT DOCUMENTS

| | | | |
|---|---|---|---|
| 3,912,752 | 10/1975 | Meiser et al. | 260/308 R |
| 3,919,284 | 11/1975 | Lin | 260/465 D |
| 3,957,847 | 5/1976 | Davidson | 260/465 D |
| 3,979,518 | 9/1976 | Klopping | 260/465.4 |
| 4,053,612 | 10/1977 | Baude et al. | 424/304 |

FOREIGN PATENT DOCUMENTS

| | | |
|---|---|---|
| 2118317 | 11/1971 | Fed. Rep. of Germany . |
| 2201063 | 7/1973 | Fed. Rep. of Germany . |
| 2312956 | 9/1973 | Fed. Rep. of Germany . |
| 2350910 | 4/1974 | Fed. Rep. of Germany . |
| 2436654 | 2/1975 | Fed. Rep. of Germany . |
| 2436655 | 2/1975 | Fed. Rep. of Germany . |
| 2431073 | 1/1976 | Fed. Rep. of Germany . |

OTHER PUBLICATIONS

German Patent Application, P2553301.1, Filed 11-27-1975, (Bayer), 8 pp.

*Primary Examiner*—Joseph Paul Brust
*Attorney, Agent, or Firm*—Sprung, Felfe, Horn, Lynch & Kramer

[57] ABSTRACT

Oxime ethers of isonitrosocyanoacetamides of the formula

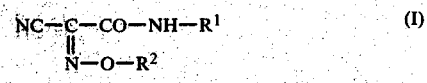

in which
R¹ represents hydrogen or the —CO—NHR³ group,
R² is optionally substituted aryl or aralkyl, or substituted methyl, and
R³ is hydrogen or alkyl with up to 4 carbon atoms, which possess fungicidal properties.

15 Claims, No Drawings

FUNGICIDALLY ACTIVE OXIME-ETHERS OF ISONITROSOCYANOACETAMIDES

The present invention relates to and has for its objects the provision of particular new oxime-ethers of isonitrosocyanacetamides which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

As has already been known for a long time, zinc ethylene-1, 2-bis-dithiocarbamate (Compound A) and N-trichloromethylthiotetrahydrophthalimide (Compound B) can be used as fungicides in agriculture and in horticulture; amongst commercially available products, the said compounds are of great importance (see R. Wegler, "Chemie der Pflanzenschutz- und Schädlingsbekämpfungsmittel" ("Chemistry of Plant Protection Agents and Pesticides"), Volume 2, pages 54 and 108, Berlin/Heidelberg/New York (1970)). However, the action is not always satisfactory if low concentrations are used. Furthermore, these fungicides cannot be employed for curative purposes.

The fungicidal action of some isonitrosocyanoacetamide derivatives is also known (see, in this context, DT-OS's (German Published Specifications) Nos. 2,118,317, 2,312,956, 2,350,910, 2,436,654 and 2,436,655 and U.S. Pat. No. 3,919,284). Here again, the activity is not reliable if low amounts are used, whereas at normal concentrations damage to the plants is observed.

The present invention now provides, as new compounds, the oxime-ethers of isonitrosocyanoacetamides and of their derivatives, of the general formula

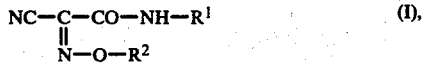

in which
$R^1$ represents hydrogen or the —CO—NHR$^3$ group, wherein
$R^3$ is hydrogen or alkyl with up to 4 carbon atoms, and
$R^2$ represents phenyl which carries one or more substituents selected from nitro, trifluoromethyl and cyano groups and optionally carries one or more halogen substituents; or represents benzyl which carries one or more substituents, on the aromatic part, selected from benzoyl, monohalogenobenzoyl, dihalogenobenzoyl, phenyl, phenoxy and alkoxy with 1 to 14 carbon atoms; or represents diphenylmethyl or triphenylmethyl, either of these radicals optionally carrying, on any of the phenyl nuclei, one or more substituents selected from phenyl, cyano, trifluoromethyl, alkyl or alkoxy within either case up to 4 carbon atoms, methylthio and halogen; or represents a doubly substituted methyl group, of which the first substituent is the tert.-butylcarbonyl radical and the second substituent is an optionally halogenated phenoxy or biphenyloxy radical; or represents cyclohexylaminocarbonyl-methyl or dicyclohexylaminocarbonylmethyl which radicals can be further substituted on the methyl radical by 1 or 2 alkyl groups each with up to 4 carbon atoms; or represents phenylaminocarbonyl-methyl or diphenylaminocarbonyl-methyl optionally substituted on the methyl radical by 1 or 2 alkyl groups each with up to 4 carbon atoms and on the phenyl nucleus by at least one of halogen and/or alkyl with up to 6 carbon atoms.

As oxime derivatives, the compounds according to the invention can exist in two different geometrical structures:

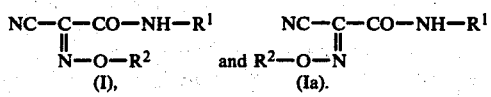

In the text which follows, the spatial structure will not be specified; for the purposes of the present application, the indicated formulae (I) are intended in every case also to embrace the corresponding formula according to spatial structure (Ia).

The compounds according to the invention exhibit a good fungicidal action. They can be used for protection, cure and even eradication and furthermore have systemic and/or locosystemic properties. Surprisingly, they exhibit better toleration by plants than the isonitrosocyanoacetamide derivatives known from the state of the art. Compared to the dithiocarbamates and N-trichloromethylthiotetrahydrophthalimide, they have the advantage of a curative and eradicative action.

The numerous possibilities of superior biological application mean that the compounds according to the invention represent a valuable enrichment of the art. A further important aspect of the present invention is that new active compounds having valuable properties in practical use are provided at a time when there is a newly arisen need for novel fungicides, owing to resistance phenomena with respect to older active compounds.

The present invention also provides a process for the preparation of a compound of the formula (I) in which an isonitrosocyanoacetamide derivative of the general formula

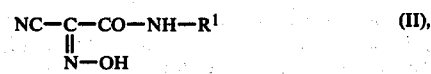

in which
$R^1$ has the abovementioned meaning, is reacted, either as such in the presence of an acid-binding agent, or in the form of an alkali metal salt, with a halogen compound of the general formula

in which
X represents chlorine, bromine or iodine and
$R^2$ has the abovementioned meaning.

If the sodium salt of isonitrosocyanoacetamide and 4-chloromethyldiphenyl are used as starting materials, the course of the reaction can be represented by the following equation:

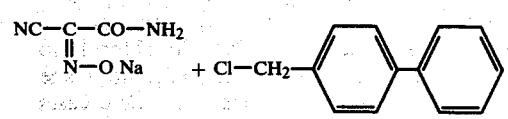

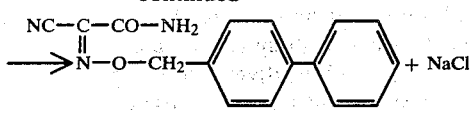

The preferred isonitrosocyanoacetamide derivatives (II) to be used as starting materials for the process according to the invention are isonitrosocyanoacetamide and isonitrosocyanoacetylurea. These compounds have already been known for a long time (see Ber. 42, pages 738, 740 and 741 (1909)).

The following should be mentioned as examples of starting compounds of the general formula (III) to be employed according to the invention: 2-nitrochlorobenzene, 1,2-dichloro-6-nitrobenzene, 2-nitro-1,4-dichlorobenzene, 2,4-dinitrochlorobenzene, 2-nitro-4-trifluoromethyl-chlorobenzene, 2,6-dinitro-4-cyano-chlorobenzene, 4-trifluoromethyl-chlorobenzene, 1,2-dichloro-4-trifluoromethylbenazene, 2,5-dichloro-3-nitro-benzonitrile, 2-cyano-4-trifluoromethylchlorobenzene, 2-trifluoromethyl-4-cyano-chlorobenzene, 2,4-dinitro-6-trifluoromethyl-chlorobenzene, 1,2,3-trichloro-5-trifluoromethyl-benzene, 2-pheny-benzyl chloride, 4-phenyl-benzyl chloride,4-benzoyl-benzyl chloride, 4-(2-,3- or 4-chlorobenzoyl)-benzyl chloride, 4-(2,3-, 2,4-, 2,5-2,6-, 3,4- or 3,5-dichlorobenzoyl)-benzyl chloride, 2-, 3- or 4-methoxybenzylbromide, 2-, 3- or 4-ethoxy-benzyl chloride, 4-isopropoxy-benzyl chloride, 2- or 4-butoxy-benzyl chloride, 4-hexyloxybenzyl chloride, 4-octyloxybenzyl chloride, 4-dodecyloxybenzyl chloride, 4-tetradecyloxybenzyl chloride; 2-, 3- or 4-phenoxybenzyl chloride; triphenylchloromethane, bis-phenyl-[(3-trifluoromethyl-, 3-cyano-, 3-chloro-, 3-fluoro, or 3-bromo)-phenyl]-chloromethane, bis-phenyl-[(2-chloro-, 2-methoxy- or 2-bromo)-phenyl]-chloro-methane, bis-phenyl[(4-fluoro-, 4-chloro-, 4-bromo-, 4-iodo-, 4-methyl, 4-tert.-butyl-, 4-methylthio- or 4-phenyl)-phenyl]chloromethane; 1-(4-chloro-phenoxy)-, 1-(2,4-dichlorophenoxy)-, 1-(4-phenyl-phenoxy)-, 1-(2-phenyl-phenoxy)- and 1-(4-phenyl-2,6-dichlorophenoxy)-1-chloro-2-oxo-3,3-dimethylbutane; N-(bromoacetyl)-cyclohexylamide, N-(2-bromo-propionyl)-cyclohexylamide, N-(2-chloroisobutyryl)-cyclohexylamide, N-(bromoacetyl)-anilide, N-(chloroacetyl)-2-ethyl-anilide, N-(chloroacetyl)-2-isopropyl-anilide, N-(chloroacetyl)-4-butyl-anilide, N-(chloroacetyl)-2,6-diethyl-anilide, N-(chloroacetyl)-4-chloro-anilide, N-(chloroacetyl)-3-chloro-anilide, N-(chloro-acetyl)-2-chloro-anilide, N-(chloroacetyl)-2,4-dichloro-anilide, N-(2-bromopropionyl)-3,4-dichloro-anilide, N-(2-bromo-2-ethylbutyryl)-3,5-dichloro-anilide, N-(2-chloroisobutyryl)-3,4-dichloro-anilide, N-(2-chloro-isobutyryl)-3,5-dichloro-anilide, N-(2-chloro-isobutyryl)-3-methyl-anilide and N,N-diphenyl-2-chloro-isobutyric acid amide.

Starting materials of the formula (III) are known and can be prepared in accordance with processes known in principle and which are customary in the laboratory. Data relating thereto are to be found in the preparative examples given later in this text.

The preparation of the compounds according to the invention, of the formula (I), is preferably carried out in the presence of a polar solvent, such as dimethylsulphoxide, dimethylformamide, dimethylacetamide, acetone methyl ethyl ketone, methylene chloride, chloroform, chlorobenzene, toluene, dioxane, tetrahydrofuran, acetonitrile, benzonitrile or ethyl acetate. In some cases, tertiary amines are also suitable as solvents, which then at the same time act as acid-binding agents.

All customary hydrogen-halide-acceptors can be used as acid-binding agents. These include alkali metal hydroxides, alkali metal carbonates and other suitable alkali metal salts. Examples to be mentioned are sodium carbonate, sodium bicarbonate, borax (disodium tetraborate) and trilithium phosphate. If the reaction is carried out in the presence of water, neutralization can be effected by adding sodium hydroxide solution, or the salts of the isonitrosocyanoacetic acid derivatives are employed a priori. Furthermore, organic acid-binding agents can be used, such as, for example, tertiary amines. In this context, triethylamine, dimethylbenzylamine, dimethylaniline, pyridine, picoline, quinoline, ethyldiisopropylamine and ethyldicyclohexylamine should be mentioned.

The reaction temperatures cam be varied with a fairly wide range. In general, the reaction is carried out at between −50° C. and +120° C., preferably between −5° C. and +80° C.

The reactions can also be carried out in mixtures of water and a water-miscible organic solvent, or in heterogeneous systems consisting of water and a water-immiscible or only partially water-miscible solvent; in these cases, the reaction temperature range is generally between the freezing point of water, or the solidification point of the aqueous solution, and 100° C., preferably from −5° to +80° C.

The reaction temperatures and reaction time are determined by the activity of the starting materials of the formula (II). Advantageously, a small amount of an iodide is added to the mixtures before the reaction, unless a compound of the formula (III) with iodine as a leaving group happens to be employed. This increases the rate of reaction and reduces the risk of formation of compounds having a nitrone structure (see, in this context, Houben-Weyl, "Methoden der organischen Chemie" ("Methods of Organic Chemistry"), volume 10/4, Stuttgart (1968)).

Depending on the working conditions, the active compounds according to the invention precipitate in a crystalline form or remain dissolved in the organic solvent and can then be separated out by cautiously concentrating the solution or by adding an organic solvent of lower polarity, such as carbon tetrachloride, cyclohexane or dibutyl ether, or, where appropriate, by adding water.

Some of the compounds according to the invention decompose at an elevated temperature; in such cases, the melting points can only be determined with a low degree of accuracy, if at all. The presence of certain structural features can, however, be deduced from the NMR spectra. The IR spectra also show characteristic absorption bands.

The active compounds according to the invention exhibit a powerful fungitoxic action. They do not harm crop plants in the concentrations required for combating fungi. For these reasons, they are suitable for use as plant protection agents for combating fungi. Fungitoxic agents are employed in plant protection for combating Plasmodiophoromycetes, Oomycetes, Chyrtridiomycetes, Zygomycetes, Ascomycetes, Basidiomycetes and Deuteromycetes.

The active compound according to the invention can be employed against parasitic fungi which attack aboveground parts of plants or which attack the plants through the soil, and against seed-borne pathogens. Accordingly, they can also be used for soil treatment and for seed treatment.

The active compounds in particular exhibit a high protective and curative activity against Phycomycetes. In addition, good actions against species of Mycosphaerella and species of Rhizoctonia, and against rust fungi, can be detected.

The active compounds according to the invention not only exhibit the good properties of outstanding commercially available preparations, but also possess additional substantial advantages. These reside above all in the ability of the compounds according to the invention to penetrate into the plant. They can be taken up by the seed surface, by the roots, and also by above-ground plant organs after external application. Furthermore, they possess the advantageous ability of becoming effective locosystemically, that is to say of exerting a depth action in the plant tissue and thereby of eliminating fungal pathogens which have already penetrated into the tissue of the host plant.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, includng emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloakanes, (e.g. cyclohexne, etc.), paraffins (e.g. petroleum or mineral oil fractions), chlorinated aliphatic hydrocarbons (e.g. methylene chloride, dichlorodifluoromethane, trichlorofluoromethane, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amines (e.g. dimethyl formamide, etc.), sulfoxides (e.g. dimethyl sulfoxide, etc.), acetonitrile ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

In addition to the above possible formulations, it should be noted that the compounds according to the invention can be formulated together wth sucrose, dextrose, dextrins, anhydrous calcium sulphate or calcium sulphate hemihydrate.

Such acitve compounds may be employed alone or in the form of mixtures with one another and/or with such solid and/or liquid dispersible carrier vehicles and/or with other known compatible active agents, especially plant protection agents, such as other fungicides, or insecticides, acaricides, nematicides, bactericides, rodenticides, herbicides, fertilizers, growth-regulating agents, bird repellents, plant nutrients, agents for improving soil structure, etc., if desired, or in the form of particular dosage preparations for specific application made therefrom, such as solutions, emulsions, suspensions, powders, pastes and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compund if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Especially in the case of use as leaf fungicides, the active compound concentrations in the use forms can be varied within a fairly wide range. They are in general between 0.5 and 0.0005 per cent by weight, preferably between 0.2 and 0.001 per cent.

In the treatment of seed, amounts of active compound of 0.01–5 g per kilogram of seed are generally required, preferably 0.5–5 g.

For the treatment of soil, amounts of active compound of 1–1,000 g per cubic meter of soil, preferably of 10–200g, are required.

Furthermore, the present invention contemplates methods of selectively killing, combating or controlling pests, e.g. fungi, which comprises applying to at least one of correspondingly (a) such fungi, and (b) the corresponding habitat thereof, i.e. the locus to be protected, e.g. to a growing crop, to an area where a crop is to be grown or to a domestic animal, a correspondingly combative or toxic amount, i.e. fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

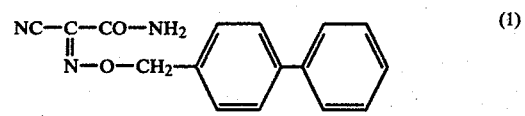

(1)

11.2 g (0.2 mol) of potassium hydroxide, dissolved in 20 ml of water, were added to 22.6 g (0.2 mol) of isonitrosocyanoacetamide in 400 ml of dimethylsulphoxide. 200 g of solvent were distilled off under a pressure of about 0.5 mm Hg. 40.6 g (0.2 mol) of 4-chloromethyl-diphenyl, dissolved in 80 ml of toluene and 100 mg of sodium iodide, were added to the residue. The mixture was then kept for 8 hours at a temperature of 80° C. The greater part of the solvent was distilled off in vacuo. The residue crystallized after addition of water. The crystals were separated off, washed with water and toluene, dried in vacuo at 70° to 80° C. and then recrystallized from 1 l of toluene. 42.5 g of 2-cyano-2-(4-phenylbenzyl)-oximinoacetamide of melting point 172.5° C. were obtained.

Spectra: IR (KBr): 3.445, 1.682, 1,653, 1,580, 842, 822, 752 and 720 cm$^{-1}$. IR (CHCl$_3$): 3,530, 3,410, 2,240, 1,710, 1,600, 1,578 and 1,562 cm$^{-1}$.

The following compounds of the formula (I) were obtained analogously:

Table 1

| Compound No. | Formula | Physical properties |
|---|---|---|
| 2 | ![structure with C$_2$H$_5$ on benzene ring, —NH—CO—CH$_2$O—N=C(CN)(CO—NH$_2$)] | Melting point 184° C. |
| 3 | ![structure with two C$_2$H$_5$ groups on benzene ring, —NH—CO—CH$_2$—O—N=C(CN)(CO—NH$_2$)] | Melting point 201.5° C. |
| 4 | ![structure with Cl, Cl on benzene ring, —NH—CO—CH$_2$—O—N=C(CN)(CO—NH$_2$)] | Melting point 216.5° C. |

Table 1-continued

| Compound No. | Formula | Physical properties |
|---|---|---|
| 5 | 2,4-Cl$_2$-C$_6$H$_3$-NH-CO-CH$_2$-O-N=C(CN)-CO-NH$_2$ | Melting point 230.5° C. |
| 6 | 2,4-Cl$_2$-C$_6$H$_3$-NH-CO-C(CH$_3$)$_2$-O-N=C(CN)-CO-NH$_2$ | Melting point 236° C. |
| 7 | C$_6$H$_5$-CO-C$_6$H$_4$-CH$_2$-O-N=C(CN)-CO-NH$_2$ | Melting point 162° C. |
| 8 | CH$_3$O-C$_6$H$_4$-CH$_2$-O-N=C(CN)-CO-NH$_2$ | Melting point 146° C. |
| 9 | CH$_3$O-C$_6$H$_4$-CH$_2$-O-N=C(CN)-CO-NH-CO-NH$_2$ | Melting point 150.5° C. |
| 10 | (C$_6$H$_5$)$_3$C-O-N=C(CN)-CO-NH$_2$ | Melting point 213.5° C. |
| 11 | (C$_6$H$_5$)$_2$(3-CF$_3$-C$_6$H$_4$)C-O-N=C(CN)-CO-NH$_2$ | Melting point 172° C. |
| 12 | (C$_6$H$_5$)$_2$(3-CF$_3$-C$_6$H$_4$)C-O-N=C(CN)-CO-NH-CO-NH$_2$ | Spectra: IR(CCl$_4$) 3,440, 3,410, 2,230 to 2,250, 1,745, 1,710–1,720, 1,650–1,675, 795, 745 and 695 cm$^{-1}$ |
| 13 | 4-CF$_3$-2-NO$_2$-C$_6$H$_3$-O-N=C(CN)-CO-NH$_2$ | Melting point 145.5° C. |

Table 1-continued

| Compound No. | Formula | Physical properties |
|---|---|---|
| 14 | 4-Cl-C6H4-O-CH(CO-C(CH3)3)-O-N=C(CN)-CO-NH2 | Melting point 102° C. |
| 15 | 4-biphenylyl-O-CH(CO-C(CH3)3)-O-N=C(CN)-CO-NH2 | Melting point 76° C. |
| 16 | 2-biphenylyl-O-CH(CO-C(CH3)3)-O-N=C(CN)-CO-NH2 | Melting point 126° C. |
| 17 | 2,4-Cl2-C6H3-O-CH(CO-C(CH3)3)-O-N=C(CN)-CO-NH2 | Melting point 100° C. |
| 18 | cyclohexyl-NH-CO-C(CH3)2-O-N=C(CN)-CO-NH2 | Melting point 200–202° C. |
| 19 | 3-phenoxy-C6H4-CH2-O-N=C(CN)-CO-NH2 | Melting point 124° C. |
| 20 | (C6H5)2N-CO-C(CH3)2-O-N=C(CN)-CO-NH2 | Melting point 178° C. |
| 21 | NC-C(=N-O-CH2-biphenylyl)-CO-NH-CO-NH-C2H5 | Melting point 181–185° C. |

Other possible compounds which may be prepared in the same way include:

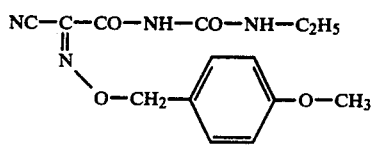

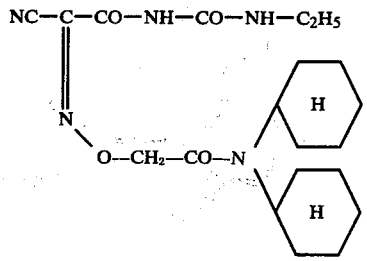

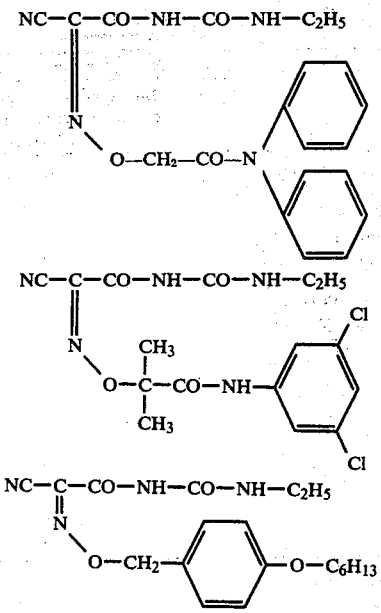

EXAMPLE 2

The preparation of the intermediates (a) 4-Chloromethyldiphenyl, of melting point 68° C., required as an intermediate in Example 1, is a compound which has already been known for a long time (see Beilstein's Handbuch der organischen Chemie (Beilstein's Handbook of Organic Chemistry), volume 5, E 11, page 505). It can be obtained from 4-phenylbenzyl alcohol and hydrochloric acid in a sealed glass tube at 100° C.

(b) The intermediates required for the preparation of Compounds 2 to 5, hereinabove are known.

(c) α-Chloro-isobutyric acid 3,5-dichloroanilide, required for the preparation of Compound 6, was prepared as follows:

53.3 g of α-chloroisobutyric acid chloride were dissolved in 200 ml of chlorobenzene. A mixture of 61.5 g of 3,5-dichloroaniline and 46 g of N,N-dimethylaniline in 300 ml of chlorobenzene was allowed to run in dropwise over the course of 35 minutes, at a temperature of −35° C. The reaction mixture was then washed at room temperature, first with dilute hydrochloric acid and then with water, and was dried over calcium chloride and concentrated in a waterpump vacuum. After adding about 200 ml of petroleum ether, crystallization occurred. The crystals were separated off, washed three times with 50 ml of petroleum ether at a time and then dried at a temperature of 73° C. and a pressure of 0.1 mm of mercury. 73.2 g of α-chloroisobutyric acid 3,5-dichloroanilide of melting point 94.5° C. were obtained.

(d) The starting compounds for the preparation of Compounds 7 to 10 and 13 are also known from the literature.

(e) The starting compound for the preparation of Compounds 11 and 12 has not yet been described in the literature and its preparation is carried out as indicated below (see German Pat. application No. P25, 53, 301.1 of Nov. 27, 1975 [Le A 16 824]:

570 kg (7.308 mol) of benzene were initially introduced into an enamelled kettle of 1,200 l capacity and subjected to "slight distillation" until the distillate passed over clear. 90 kg (556 mol) of anhydrous iron (III) chloride were introduced while stirring. 133 kg (506 mol) of m-trifluoromethylbenzotrichloride were allowed to run in, via a feed vessel, over the course of 3 hours at 25° C. to 30° C. internal temperature. The reaction started immediately, with evolution of hydrogen chloride. Stirring was continued for 5 hours at 25° C. to 30° C. 260 kg of ice and 260 kg of concentrated hydrochloric acid were then introduced into an enamelled kettle of 2,000 l capacity. The reaction batch was forced into the 2,000 l kettle, while stirring. The mixture was thoroughly stirred for 10 minutes and the lower aqueous phase was then separated off. The organic phase was filtered through a pressure filter, then separated from remnants of the aqueous phase, and twice stirred thoroughly with 100 kg of concentrated hydrochloric acid at a time, for 2 hours. After separating off the aqueous phase, the organic phase was distilled under a pressure of 80 to 100 mg Hg at 70° C. jacket temperature until no further benzene passed over, and a final vacuum of about 13 mm Hg had been reached. 163 kg (93% of theory) of diphenyl-(3-trifluoromethylphenyl)-methyl chloride remained, as the distillation residue, in the form of a light brown very viscous oil. A sample of the chloride had a boiling point (0.3 mm Hg) of 150° to 155° C.

(f) The starting compounds of the preparation of active Compounds 15 and 17 are known (DT-OS (German Published Specification) No. 2,431,073, pages 13 and 14, and DT-OS 2,201,063, pages 40 and 41). The synthesis of Compounds 14 and 16 is carried out analogously.

EXAMPLE 3

Mycelium growth test

Nutrient medium used:
 20 parts by weight of agar-agar
 200 parts by weight of potato decoction
 5 parts by weight of malt
 15 parts by weight of dextrose
 5 parts by weight of peptone
 2 parts by weight of disodium phosphate
 0.3 part by weight of calcium nitrate
Composition of the solvent mixture:
 0.19 part by weight of acetone
 0.01 part by weight of emulsifier (alkylaryl polyglycol ether)
 1.80 parts by weight of water
Ratio of solvent mixture to nutrient medium:
 2 parts by weight of solvent mixture
 100 parts by weight of agar nutrient medium The amount of active compound required for the desired active compound concentration in the nutrient medium was mixed with the stated amount of solvent. The concentrate was thoroughly mixed, in the stated proportion, with the liquid nutrient medium (which had been cooled to 42° C.) and was then poured into Petri dishes of 9 cm diameter. Control plates to which the preparation had not been added were also set up.

When the nutrient medium had cooled and solidified the plates were inoculated with the species of fungi stated in Table A and incubated at about 21° C.

Evaluation was carried out after 4–10 days, dependent upon the speed of growth of the fungi. When evaluation was carried out the radial growth of the mycelium on the treated nutrient media was compared with the growth on the control nutrient medium. In the evaluation of the fungus growth, the following characteristic values were used:

1 no fungus growth
up to 3 very strong inhibition of growth
up to 5 medium inhibition of growth
up to 7 slight inhibition of growth
9 growth equal to that of untreated control.

The active compounds, the active compound concentrations and the results can be seen from Table 2:

Table 2

| Active compounds | Active compound concentration 10 ppm | Mycelium growth test | | | |
|---|---|---|---|---|---|
| | | *Pythium ultimum* | *Phytophthora cactorum* | *Rhizoctonia solani* | *Mycosphaerella musicola* |
| NC—C—CO—NH$_2$<br>‖<br>NOH (B) | (known) | 9 | 9 | 9 | 9 |
| (1) | | — | 5 | 1 | 1 |
| (2) | | 5 | — | 1 | — |
| (3) | | 5 | 5 | — | — |
| (7) | | 1 | 1 | 1 | 1 |
| (4) | | — | 1 | 3 | 5 |
| (5) | | — | 1 | 5 | — |
| (8) | | 2 | 1 | 1 | 1 |
| (9) | | — | 1 | 1 | — |
| (19) | | 2 | 1 | 1 | 1 |

Table 3

Phytophthora test (tomatoes)/protective

| Active compound | Infection in % at an active compound concentration of 0.0025% |
|---|---|
| CH$_2$—NH—CS—S<br>\|            >Zn<br>CH$_2$—NH—CS—S<br>(known) (A) | 41 |
| NC—C—CO—NH$_2$<br>‖<br>N—O—CH$_3$<br>(known) (C) | 7 |
| (1) | 10 |
| (2) | 19 |
| (13) | 7 |
| (6) | 2 |
| (5) | 22 |
| (14) | 0 |
| (15) | 14 |
| (16) | 5 |
| (17) | 1 |
| (18) | 10 |

EXAMPLE 4

Phytophthora test (tomatoes)/protective

Solvent: 4.7 parts by weight of acetone
Emulsifier: 0.3 part by weight of alkylaryl polyglycol ether
Water: 95 parts by weight The amount of the active compound required for the desired concentration of the active compound in the spray liquid was mixed with the stated amount of solvent and the concentrate was diluted with the stated amount of water which contained the stated additions.

Young tomato plants with 2 to 4 foliage leaves were sprayed with the spray liquid until dripping wet. The plants remained in a greenhouse for 24 hours at 20° C. and at a relative atmospheric humidity of 70%. The tomato plants were then inoculated with an aqueous spore suspension of *Phytophthora infestans*. The plants were brought into a moist chamber with an atmospheric humidity of 100% and a temperature of 18°–20° C.

After 5 days the infection of the tomato plants was determined. The assessment data were converted to percent infection: 0% meant no infection; 100% meant that the plants were totally infected.

The active compounds, the concentrations of the active compound and the results can be seen from Table 3:

EXAMPLE 5

Phytophthora test (tomatoes)/curative

Solvent: 4.7 parts by weight of acetone
Emulsifier: 0.3 part by weight of alkylaryl polyglycol ether
Water: 95 parts by weight The amount of the active compound required for the desired concentration of the active compound in the spray liquid was mixed with the stated amount of solvent and the concentrate was diluted with the stated amount of water which contained the stated additions.

Young tomato plants with 2 to 4 foliage leaves were inoculated with an aqueous spore suspension of *Phytophthora infestans*. The plants remained for 7 hours at 20° C. and a relative atmospheric humidity of 100%.

After a short drying-off time, the plants were sprayed with the spray liquid, prepared in the manner described above, until dripping wet, and were then brought into a moist chamber at 100% atmospheric humidity and 18° to 20° C.

After 5 days the infection of the tomato plants was determined. The assessment data were converted to percent infection: 0% meant no infection; 100% meant that the plants were totally infected.

The active compounds, the concentrations of the active compound and the results can be seen from Table 4:

Table 4

Phytophthora test (tomatoes)/curative

| Active compound | Infection in % at an active compound concentration of 0.025% |
|---|---|
| $CH_2-NH-CS-S$<br>$\quad\quad\quad\quad\quad\quad\quad >Zn$<br>$CH_2-NH-CS-S$<br>(known) (A) | 61 |
| $NC-C-CO-NH_2$<br>$\quad\;\;\parallel$<br>$\quad\;\;NOH$<br>(known) (B) | 7 |
| (1) | 2 |
| (2) | 6 |
| (3) | 0 |
| (7) | 0 |
| (13) | 1 |
| (4) | 0 |
| (6) | 7 |
| (10) | 4 |
| (14) | 6 |
| (15) | 0 |
| (16) | 0 |
| (17) | 1 |

EXAMPLE 6

Shoot treatment test/cereal rust/protective (leaf-destructive mycosis)

To produce a suitable preparation of active compound, 0.25 part by weight of active compound was taken up in 25 parts by weight of dimethylformamide and 0.06 part by weight of alkylaryl polyglycol ether emulsifier and then 975 parts by weight of water were added. The concentrate was diluted with water to the desired final concentration of the spray liquor.

To test the protective activity, one-leaved young wheat plants of the "Jubilar" variety were inoculated with a uredospore suspension of Puccinia recondita in 0.1% strength aqueous agar. After the spore suspension had dried on, the wheat plants were sprayed with the preparation of active compound until dew-moist and were placed, for incubation, in a greenhouse for 24 hours at about 20° C. and 100% relative atmospheric humidity.

After 20 days' dwell time of the plants at a temperature of 20° C. and 80–90% atmospheric humidity, the occurrence of rust pustules on the plant was evaluated. The degree of infection was expressed as a percentage of the infection of the untreated control plants. 0% denoted no infection and 100% denoted the same degree of infection as in the case of the untreated control. The active compound was the more active, the lower was the degree of rust infection.

The active compounds, active compound concentrations in the spray liquor and degrees of infection can be seen from Table 5:

Table 5

Shoot treatment test/cereal rust/protective

| Active compounds | Active compound concentration in the spray liquor in % by weight | Infection in % of the untreated control |
|---|---|---|
| (1) | 0.025 | 25 |
| (2) | 0.025 | 0 |
| (3) | 0.025 | 0 |
| (7) | 0.025 | 25 |
| (13) | 0.025 | 12.5 |
| (4) | 0.025 | 12.5 |
| (6) | 0.025 | 25 |
| (8) | 0.025 | 12.5 |
| (9) | 0.025 | 25 |
| (10) | 0.025 | 25 |

Table 5-continued

Shoot treatment test/cereal rust/protective

| Active compounds | Active compound concentration in the spray liquor in % by weight | Infection in % of the untreated control |
|---|---|---|
| (18) | 0.025 | 12.5 |
| (15) | 0.025 | 12.5 |
| (19) | 0.025 | 12.5 |
| (16) | 0.025 | 0 |

EXAMPLE 7

Phytotoxicity test

Solvent: 4.7 parts by weight of acetone
Emulsifier: 0.3 part by weight of alkylaryl polyglycol ether
Water: 95 parts by weight The amount of active compound required for the desired concentration of the active compound in the spray liquor was mixed with the stated amount of the solvent and the concentrate was diluted with the stated amount of water, which contained the stated additives. Young tomatoes were sprayed with the spray liquor until dripping wet. After drying off, the plants were set up in a greenhouse at a temperature of +20° C. and about 70% relative atmospheric humidity.

The damage to the plants was evaluated repeatedly. The evaluation was made in accordance with a scheme of rating from 1 to 9.

1 denoted no damage
9 denoted that the plants were totally damaged or dead. The period of observation was as a rule 4 days.

The active compounds, active compound concentrations and results can be seen from Table 6:

Table 6

Phytotoxicity test

| Active compound | Damage at an active compound concentration of 0.2% |
|---|---|
| $NC-C-CO-NH_2$<br>$\quad\;\;\parallel$<br>$\quad\;\;NOH$<br>(known) (B) | 8 |
| (1) | 1 |
| (2) | 3 |
| (7) | 1 |
| (13) | 4 |
| (6) | 2 |
| (5) | 1 |
| (10) | 3 |

The process of the present invention is illustrated by the following preparative Examples.

It will be appreciated that the instant specification and examples are set forth by way of illustration and not limitation, and that various modifications and changes may be made without departing from the spirit and scope of the present invention.

What is claimed is:

1. An oxime-ether of isonitrosocyanoacetamide of the formula

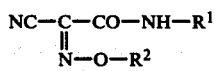

in which $R^1$ represents hydrogen or the —CO—NHR$^3$ group, wherein $R^3$ is hydrogen or alkyl with up to 4 carbon atoms, and $R^2$ represents phenyl which carries one or more substituents selected from nitro, trifluoromethyl and cyano groups and optionally carries one or more halogen substituents; or represents benzyl which carries one or more substituents, on the aromatic part, selected from benzoyl, monohalogenobenzoyl dihalogenobenzoyl, phenyl and alkoxy with 1 to 14 carbon atoms; or represents phenylaminocarbonyl-methyl or diphenylaminocarbonyl-methyl optionally substituted on the methyl radical by 1 or 2 alkyl groups each with up to 4 carbon atoms and on the phenyl nucleus by at least one of halogen and /or alkyl with up to 6 carbon atoms.

2. An ether according to claim 1, in which $R^1$ represents hydrogen or the —CO—NH$_2$ group and $R^2$ represents a phenyl radical carrying 1 to 3 substituents selected from nitro and trifluoromethyl groups, which phenyl radical can also be chlorine-substituted; or represents a benzyl radical which is substituted in the aromatic part by phenyl, benzoyl, monochlorobenzoyl, dichlorobenzoyl or alkoxy with up to 14 carbon atoms; or represents the phenylaminocarbonylmethyl, 1-(phenylaminocarbonyl)-ethyl or 2-(phenylaminocarbonyl)-isopropyl group, the aromatic part of which can optionally carry up to 2 chlorine atoms and up to 2 alkyl radicals each with up to 4 carbon atoms as substituents.

3. An ether according to claim 1 wherein such ether is 2-cyano-2-(4-phenylbenzyl)-oximinoacetamide of the formula

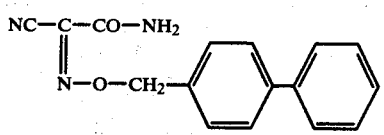

4. An ether according to claim 1 wherein such ether is 2-cyano-2-(3-nitro-4-trifluoromethyl-phenyl)-oximinoacetamide of the formula

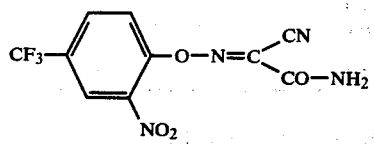

5. An ether according to claim 1 wherein such ether is 2-cyano-2-(3,4-dichlorophenylaminocarbonymethyl)-oximinoacetamide of the formula

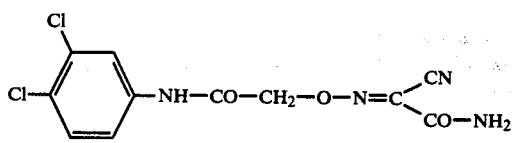

6. An ether according to claim 1 wherein such ether is 2-cyano-2-(dimethyl-(3,5-dichlorophenylaminocarbonyl-methyl)-oximinoacetamide of the formula

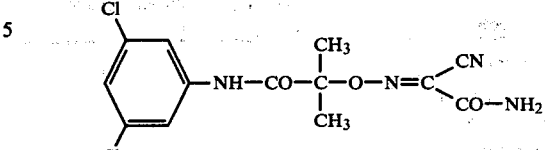

7. An ether according to claim 1 wherein such ether is 2-cyano-2-(4-benzoylbenzyl)-oximinoacetamide of the formula

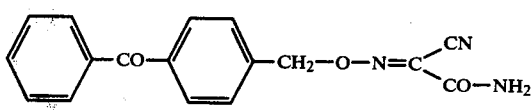

8. An ether according to claim 1 wherein such ether is 2-cyano-2-(4-methoxylbenzyl)-oximinoacetamide of the formula

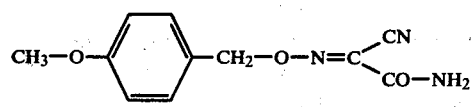

9. An ether according to claim 1 wherein such ether is 2-cyano-2-(4 methoxybenzyl)-oximinoacetylurea of the formula

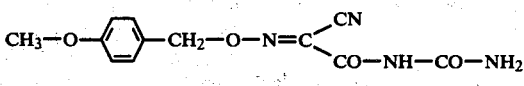

10. An ether according to claim 1, in which $R^2$ represents phenylaminocarbonylmethyl, which can be substituted at the methyl radical by 1 or 2 alkyl groups each with up to 4 carbon atoms and at the phenyl nucleus by at least one of halogen and alkyl with up to 6 carbon atoms.

11. An ether according to claim 1, in which $R^2$ represents 2-(phenylaminocarbonyl)-isopropyl substituted on the phenyl nucleus by at least one of halogen and alkyl with up to 6 carbon atoms.

12. An ether according to claim 1, in which $R^2$ represents phenylaminocarbonylmethyl substituted on the phenyl nucleus by at least one of halogen and alkyl with up to 6 carbon atoms.

13. A fungicidal composition containing as active ingredient a fungicidally effective amount of an ether according to claim 1 in admixture with a diluent.

14. A method of combating fungi which compriss applying to the fungi, or to a habitat thereof, a fungicidally effective amount of an ether according to claim 1.

15. The method according to claim 14 in which said ether is:
2-cyano-2-(4-phenylbenzyl)-oximinoacetamide,
2-cyano-2(3-nitro-4-trifluoromethyl-phenyl)-oximinoacetamide,
2-cyano-2-(3,4-dichlorophenylaminocarbonylmethyl)-oximinoacetamide,
2-cyano-2-(4-benzoylbenzyl)-oximinoacetamidem
2-cyano-2-(4-methoxybenzyl)-oximinoacetamide, or
2-cyano-2-(4-methoxybenzyl)-oximinoacetylurea.

* * * * *